United States Patent [19]
Takada et al.

[11] Patent Number: 5,622,657
[45] Date of Patent: Apr. 22, 1997

[54] PROLONGED RELEASE MICROPARTICLE PREPARATION AND PRODUCTION OF THE SAME

[75] Inventors: Shigeyuki Takada, Salt Lake City, Utah; Yoshiaki Uda, Takarazuka; Yasuaki Ogawa, Ohyamazaki-cho, both of Japan

[73] Assignee: Takeda Chemical Industries, Ltd., Osaka, Japan

[21] Appl. No.: 455,546

[22] Filed: May 31, 1995

Related U.S. Application Data

[62] Division of Ser. No. 387,392, Feb. 13, 1995, which is a continuation of Ser. No. 953,679, Oct. 1, 1992, abandoned.

[30] Foreign Application Priority Data

Oct. 1, 1991 [JP] Japan .................................. 3-253517

[51] Int. Cl.$^6$ .......................... B01J 13/04; B01J 13/22
[52] U.S. Cl. ............................................. 264/4.32; 264/4.6
[58] Field of Search .................................. 264/4.32, 4.6

[56] References Cited

U.S. PATENT DOCUMENTS

| | | | |
|---|---|---|---|
| 3,336,155 | 8/1967 | Rowe | 427/212 |
| 4,187,194 | 2/1980 | Wellman et al. | 427/213.36 |
| 4,486,436 | 12/1984 | Schmidt et al. | 514/263 |
| 4,637,905 | 1/1987 | Gardner | 264/4.3 |
| 4,654,441 | 3/1987 | Okada et al. | 564/38 |
| 4,675,189 | 6/1987 | Kent et al. | 424/490 |
| 4,878,094 | 10/1989 | Benton et al. | 264/4.3 |
| 5,049,384 | 9/1991 | Howard et al. | 264/4.3 |
| 5,093,130 | 3/1992 | Fuji et al. | 264/4.3 |

FOREIGN PATENT DOCUMENTS

| | | |
|---|---|---|
| 101891 | 3/1984 | European Pat. Off. . |
| 190833 | 8/1986 | European Pat. Off. . |
| 266909 | 5/1988 | European Pat. Off. . |
| 315875 | 5/1989 | European Pat. Off. . |
| 505966 | 9/1992 | European Pat. Off. . |
| 580428A1 | 1/1994 | European Pat. Off. . |
| 580428 | 1/1994 | European Pat. Off. . |
| 2073431 | 10/1971 | France . |
| 3916020 | 11/1990 | Germany . |
| 51-123815 | 4/1975 | Japan . |
| 1287475 | 8/1972 | United Kingdom . |

OTHER PUBLICATIONS

Bodmeier et al., "Preparation Of Biodegradable Poly(±)lactide Moroparticles Using a Spray–Drying Technique", J. Pharm. Pharmacol., 1988, vol. 40, pp. 764–767.

*Primary Examiner*—Nathan M. Nutter
*Attorney, Agent, or Firm*—Foley & Lardner

[57] ABSTRACT

A novel microparticle preparation comprising microparticles of a polymer which contain a drug and are coated with a film of an agent for preventing aggregation of the microparticles is disclosed. The preparation is produced by spraying a solution of a polymer containing a drug and an aqueous solution of an agent for preventing aggregation of the microparticles separately from different nozzles and contacting them with each other in a spray dryer.

15 Claims, No Drawings

PROLONGED RELEASE MICROPARTICLE PREPARATION AND PRODUCTION OF THE SAME

This application is a division of application Ser. No. 08/387,392, filed Feb. 13, 1995, which is a continuation of application Ser. No. 07/953,679, filed Oct. 1, 1992 and now abandoned.

FIELD OF THE INVENTION

The present invention relates to a microparticle preparation comprising microparticles of a polymer which contain a drug and are coated with a film of an agent for preventing aggregation of the microparticles (hereinafter sometimes referred to as a microparticle preparation) and the production thereof by spray drying.

BACKGROUND OF THE INVENTION

Various dosage forms have meet proposed for drugs which require long-term repeated administration. For example, JP-A 57-118512 (U.S. Pat. No. 4,675,189) discloses microencapsulation of a drug by phase separation process using a coacervation agent such as mineral oils, vegetable oils or the like. However, the microcapsules obtained by this technique have a disadvantage that they tend to readily adhere to each other with low-shear in the course of production. Further, the large scale production thereof is difficult because a lot of solvent is used.

The traditional microencapsulation method which comprises formation of a three-phase emulsion containing a drug, followed by microencapsulation thereof by an in-water drying process to obtain microcapsules is mentioned in JP-A 60-100516 (U.S. Pat. No. 4,652,441). Although this technique improves the above disadvantage of adhesion, some points to be improved still remain. Namely, it is difficult to obtain microcapsules having a high drug content because, in the case of a water-soluble drug, the drug leaks out to the outer aqueous phase and the entrapping ratio thereof drops. In the case of both water-soluble and fat-soluble drugs, the in water drying process takes a long period of time, and a freeze-drying step is essential for pulverization. Further, in general, the microcapsules thus obtained have a large initial release rate of a drug. Furthermore, the microcapsules tend no be readily influenced by scaling up of the production and large scale treatment is difficult.

On the other hand, there are reports relating to microencapsulation by spray drying with one nozzle. However, in these reports, the initial release rate of a drug is large. In addition the desired prolonged release over a long period of time is not achieved and there is a problem that the large amount of microcapsules often aggregate to each other and adhere to a spray dryer.

OBJECTS OF THE INVENTION

The main object of the present invention is to provide an improved prolonged release microparticle preparation wherein the above problems in conventional prolonged release microcapsules, such as aggregation of each other and adhesion to a spray dryer, are minimized.

Another object of the present invention is to provide a process for the production of such an improved prolonged release microparticle preparation.

These objects as well as other objects and advantages of the present invention will become apparent to those skilled in the art from the following description.

SUMMARY OF THE INVENTION

Under these circumstances, the present inventors have intensively researched to develop prolonged release preparations of water-soluble or fat-soluble drugs. As a result, it has been found that microcapsules having a high entrapping ratio of a drug, a small initial release rate of a drug and excellent properties can be obtained efficiently and continuously in large amounts and in a short period of time by atomizing and spraying: (1) a solution containing a drug and a polymer, (2) a water-in-oil (W/O) type emulsion whose internal phase is a solution containing a water-soluble drug and whose external phase is a solution containing a polymer or (3) a solid-in-oil (S/O) type suspension containing finely divided particles of a drug from one nozzle of a spray dryer (e.g. two-fluid nozzle, multi-fluid nozzle or pressure nozzle or rotary disc for two-liquid spraying) and by spraying a solution of an agent for preventing aggregation of microcapsules from the other nozzle. After further studies based on this finding, the present invention has been completed.

The present invention provides a microparticle preparation comprising microparticles of a polymer which contain a drug and are coated with a film of an agent for preventing aggregation of the microparticles.

Further, the present invention provides a process for the production of a microparticle preparation comprising, spraying a solution of a polymer containing a drug and an aqueous solution of an agent for preventing aggregation of the microparticles separately from different nozzles and contacting them with each other in a spray dryer to produce microparticles of the polymer which contain the drug and are coated with a film of the agent for preventing aggregation of the microparticles.

According to the present invention, it is possible to produce a microparticle preparation having a desired and strong structure with minimizing loss of a drug by spray-drying the solution, emulsion or suspension containing a drug and a polymer by using a spray dryer to volatilize water as well as an organic solvent. Further, it is possible to reduce the initial release rate of a drug to a smaller amount than that of the in-water drying process. Furthermore, it is possible to obtain powder particles having excellent fluidity in a short period of time without employing any freeze-drying step. This is achieved by spraying a solution of an agent for preventing aggregation of microparticles (hereinafter referred to as "aggregation-preventing agent") from another nozzle at the same time to coat the surface of the microparticles with the aggregation-preventing agent, thereby preventing aggregation of the microparticles each other and adhesion of the microparticles to a spray dryer.

DETAILED DESCRIPTION OF THE INVENTION

Examples of the microparticle preparation include a microcapsule and the like. Most preferred examples include a microcapsule.

As the aggregation-preventing agent, in general, there can be used water-soluble materials which are applicable to human, solid at room temperature (about 15° to 25° C.) and non-adhesive in their dried state. Examples thereof include water-soluble saccharides such as mannitol, sorbitol, lactose, glucose, sucrose, starch (e.g., corn starch, potato starch, etc.) and the like; amino acids (e.g., glycine, phenylalanine, etc.); proteins (e.g., gelatin, fibrin, collagen, albumin, etc.); water-soluble cellulose (e.g., crystalline cellulose, carboxymethyl cellulose and the like and salts thereof, etc.); and the like. These can be used alone or in combination with each other. Among water-soluble saccharides can be advantageously used. Among water-soluble saccharides, mannitol can be advantageously used.

The weight ratio of the aggregation-preventing agent to the polymer can be in a range wherein the desired aggregation-preventing effect is obtained, and is about 0.1 to about 100 times, preferably 0.1 to 50 times, more preferably 0.2 to 10 times the weight of the polymer.

The drug to be used in the present invention is not specifically limited. Examples thereof include peptides having biological activities, other antibiotics, antitumor agents, antipyretics, analgesics, anti-inflammatory agents, antitussive expectorants, sedatives, muscle relaxants, antiepileptic agents, antiulcer agents, antidepressants, antiallergic agents, cardiotonics, antiarrhythmic agents, vasodilators, hypotensive diuretics, antidiabetic agents, anticoagulants, hemostatics, antituberculous agents, hormone preparations, narcotic antagonists, bone resorption inhibitors, angiogenesis-inhibiting substances and the like.

The peptides having biological activities to be used in the invention are those having two or more amino acids, preferably having molecular weight of about 200 to 80,000.

Examples of the peptide include luteinizing hormone-releasing hormone (LH-RH), its derivatives having similar activity, i.e., a peptide of the the formula (I):

(Pyr)Glu-R$_1$-Trp-Ser-R$_2$-R$_3$-R$_4$-Arg-Pro-R$_5$    (I)

wherein R$_1$ is His, Tyr, Trp or p-NH$_2$-Phe; R$_2$ is Tyr or Phe; R$_3$ is Gly or D-amino acid residues; R$_4$ is Lue, Ile or Nle; and R$_5$ is Gly-NH-R$_6$ (wherein R$_6$ is H or lower alkyl optionally substituted with a hydroxy group) or NH-R$_6$ (wherein R$_6$ is as defined above), or salts thereof [see, U.S. Pat. Nos. 3,853,837, 4,008,209 and 3,972,859; G.B. Patent No. 1,423,083; and Proc. Nat. Acad. Sci. U.S.A., vol. 78, pp. 6509–6512 (1981)].

As the D-amino acid residue represented by R$_3$ in the above formula (I), there are, for example, α-D-amino acids having up to 9 carbon atoms (e.g., Lue, Ile, Nle, Val, NVal, Abu, Phe, Phg, Set, Tyr, Met, Ala, Trp, α-Aibu, etc.) and the like. These residues may have suitable protective groups (e.g., t-butyl, t-butoxy, t-butoxycarbonyl, etc.). The acid addition salts and metal complexes of the peptide of the formula (I) [hereinafter referred to as the peptide (I)] can be used in the same manner as the peptide (I).

The abbreviations of amino acids, peptides, protective groups, etc. in the peptide (I) are those established by IUPAC-IUB Commission on Biochemical Nomenclature or those commonly used in the art. When optical isomers of amino acids are present, the amino acids are represented as L-isomers unless otherwise indicated.

In the present specification, the acetic acid salt of the peptide (I) wherein R$_1$ is His, R$_2$ is Tyr, R$_3$ is D-Leu, R$_4$ is Leu and R$_5$ is NHCH$_2$-CH$_3$ is referred to as "TAP-144". The general name of the acetic acid salt of the peptide is leuprorelin. Other LH-RH analogues include nafarelin; (pyro)Glu-His-Trp-Ser-Tyr-(3-naphtyl)-D-Ala-Leu-Arg-Pro-GluNH$_2$, goserelin; (pyro)Glu-His-Trp-Ser-Tyr-O-tert-bytyl-D-Ser-Leu-Arg-Pro-semicarbazide or salt thereof.

Examples of the peptide (I) include LH-RH antagonists (see, U.S. Pat. Nos. 4,086,219, 4,124,577, 4,253,997, 4,317, 815, 329,526 and 368,702).

Further examples of the peptides having biological activities include oligopeptides such as insulin, somatostatin, somatostatin derivatives (see, U.S. Pat. Nos. 4,087,390, 4,093,574, 4,100,117 and 4,253,998), growth hormone, prolactin, adrenocorticotropic hormone (ACTH), melanocyte-stimulating hormone (MSH), thyrotropin-releasing hormone (TRH), their salts and derivatives (see, JP-A 50-221273, JP-A 52-116465), thyroid-stimulating hormone (TSH), luteinizing hormone (LH), follicle-stimulating hormone (FSH), vasopressin, vasopressin derivatives (desmopressin [see, Folia Endocrinologica Japonica, vol. 54, no. 5, pp. 676–691 (1978)]), oxytocin, calcitonin, parathyroid hormone, glucagon, gastrin, secretin, pancreozymin, cholecystokinin, angiotensin, human placental lactogen, human chorionic gonadotropin (HCG), enkephalin, enkephalin derivatives (see, U.S. Pat. No. 4,277,394 and EP-A 31,567); and polypeptides such as endorphin, kyotorphin, interferon (α-type, β-type, γ-type), interleukin (I to XI), tuftsin, thymopoietin, thymosin, thymosthymlin, thymic humoral factor (THF), serum thymic factor (FTS) and derivatives thereof (see, U.S. Pat. No. 4,229,438) and other thymic factors [Medicine in Progress, vol. 125, no. 10, pp. 835–843 (1983)], tumor necrosis factor (TNF), colony stimulating factor (CSF), motilin, deinorphin, bombesin, neurotensin, caerulein, bradykinin, urokinase, asparaginase, kallikrein, substance P, nerve growth factor, blood coagulation factor VIII and IX, iysozyme chloride, polymyxin B, colistin, gramicidin, bacitracin, protein synthesis-stimulating peptide (G.B. Patent No. 8,232,082), gastric inhibitory polypeptide (GIP), vasoactive intestinal polypeptide (VIP), platelet-derived growth factor (PDGF), growth hormone-releasing factor (GRF, somatoclinine), bone morphagenetic protein (BMP), epidermal growth hormone (EGF), erythropoietin (EPO) and the like.

Examples of the above antitumor agent include bleomycin hydrochloride, methotrexate, actinomycin D, mitomycin C, vinblastine sulfate, vincristine sulfate, daunorubicin hydrochloride, adriamycin, neocarzinostatin, cytosine arabinoside, fluorouracil, tetrahydrofuryl-5-fluorouracil, picibanil, lentinan, levamisole, bestatin, azimexon, glycyrrhizin, poly I:C, poly A:U, poly ICLC, Cisplatin and the like.

Examples of the above antibiotics include gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cefalotin, cefaloridine, cefotiam, cefsulodin, cefmenoxime, cefmetazole, cefazolin, cefataxime, cefoperazone, ceftizoxime, moxolactam, thienamycin, sulfazecin, azusleonam, salts thereof and the like.

Examples of the above antipyretic, analgesic and anti-inflammatory agent include salicylic acid, sulpyrine, flufenamic acid, diclofenac, indometacin, morphine, pethidine, levorphanol tartrate, oxymorphone and the like.

Examples of the antitussive expectorant include ephedrine, methylephedrine, noscapine, codeine, dihydrocodeine, alloclamide, chlorphezianol, picoperidamine, cloperastine, protokylol, isoproterenol, salbutamol, terebutaline, salts thereof and the like.

Examples of the sedative include chlorpromazine, prochlorperazine, trifluoperazine, atropine, scopolamine, salts thereof and the like.

Examples of the muscle relaxant include pridinol, tubocurarine, pancuronium and the like.

Examples of the antiepileptic agent include phenytoin, ethosuximide, acetazolamide, chlordiazepoxide and the like.

Examples of the antiulcer agent include metoclopramide, histidine and the like.

Examples of the antidepressant include imipramine, clomipramine, noxiptiline, phenelzine and the like.

Examples of the antiallergic agent include diphenhydramine hydrochloride, chlorpheniramine malate, tripelennamine hydrochloride, methdilazine hydrochloride, clemizole hydrochloride, diphenylpyraline hydrochloride, methoxyphenamine hydrochloride and the like.

Examples of the cardiotonic include transpieoxocamphor, terephylol, aminophylline, etilefrine and the like.

Examples of the antiarrhythmic agent include propranolol, alprenolol, bufetololoxyprenolol and the like.

Examples of the vasodilator include oxyfedrine, diltiazem, tolazoline, hexobendine, bamethan and the like.

Examples of the hypotensive diuretic include hexamethonium bromide, pentolinium, mecamylamine, ecarazine, clonidine and the like.

Examples of the antidiabetic agent include glymidine, glipizide, phenformin, buformin, metformin and the like.

Examples of the anticoagulant include heparin, citric acid and the like.

Examples of the hemostatic include thromboplastin, thrombin, menadione, acetomenaphthone, ε-aminocaproic acid, tranexamic acid, carbazochrome sulfonate, adrenochrome monoaminoguanidine and the like.

Examples of the antituberculous agent include isoniazid, ethambutol, para-aminosalicylic acid and the like.

Examples of the hormone preparations include prednisolone, dexamethasone, betamethasone, hexoestrol, methymazole and the like.

Examples of the narcotic antagonist include levallorphan, nalorphine, naloxone, salts thereof and the like.

Example of the bone resorption inhibitors include (sulfurcontining alkyl)aminomethylenebispholphonic acid and the like.

Example of the angiogenesis-inhibiting substances include angiostatic steroid [Science, 221, 719 (1983)], fumagillin (e.g., EP-A-325199, etc.), fumagillol derivatives (e.g., EP-A-357061, EP-A-359036, EP-A-386667, EP-A-415294, etc.) and the like.

Among these drugs, the present invention can be preferably applicable to a water-soluble drug, since a water-soluble drug is apt to be released excessively at the initial stage of administration.

The solubility in water of the water-soluble drug of the present invention depends on an n-octanol/water partition coefficient.

In the present invention, an n-octanol/water partition coefficient of the water-soluble drug is preferably not more than 1, more preferably not more than 0.1.

The oil/water partition coefficient can be determined by the method described in Robert E. Notari "Biopharmaceutics and Pharmacokinetics", Marcel Dekker Inc., 1975, New York, U.S.A.. Thus, equal amount of n-octanol and a buffer solution (pH 5.5) are placed in a test tube to give a 1:1 mixture. The buffer solution is exemplified by Sorensen buffer [Ergebniss der Physiology 12, 393 (1912)], Clark-Lubs buffer [Journal of Bacteriology 2, (1), 109, 191 (1971)], Macllvaine buffer [Journal Biological Chemistry 49, 183 (1921)], Michaelis buffer [Die Wasser-Stoffionen-konzentration, p. 186 (1914)], Kolthoff buffer [Biochemische Zeitschrift 179, 410 (1926)] and so on.

An adequate amount of the drug to be tested is added to the mixture, and the test tube is stoppered, immersed in a constant-temperature bath (25° C.) and shaken vigorously. When it appears that the drug has been dissolved in between both the liquid layers and an equilibrium has been reached, the mixture is allowed to stand or is centrifuged, and aliquots of the upper and lower liquid layers are pipetted separately and analyzed for the concentration of the drug in each layer. The ratio of the concentration of the drug in the n-octanol layer to the concentration of the drug in the aqueous layer is the oil/water partition coefficient.

These water soluble drugs themself and their pharmaceutically acceptable salts can be used in the present invention.

Examples of the pharmaceutically acceptable salts of the drugs include a salt with an inorganic acid (e.g., hydrochloric acid, sulfuric acid, nitric acid, etc.), a salt with an organic acid (e.g., carbonic acid, citric acid, etc.), when the drugs have a basic residue such as amino group and so on. Examples of the pharmaceutically acceptable salts of the drugs include a salt with an inorganic base [e.g., alkaline metal such as sodium, photassium and so on, organic basic compound (e.g., triethylamine, etc.), basic amino acid (e.g., arginine, etc.) and so on], when the drugs have an acidic residue such as carboxyl group and so on.

The amount of the above drug to be used depends upon the particular kind of drug, the desired pharmacological activity, the duration time and the like. In the case of a W/O emulsion, the concentration of the drug in an internal aqueous phase is about 0.001% to about 70% (w/w), preferably 0.01% to 50% (w/w).

The polymer in the present invention is slightly water-soluble or water-insoluble, and has biocompatiblity.

"Slightly water-soluble" means that solubility of the polymer in water is not exceeding about 3% (w/w).

The amount of the polymer to be used depends upon a particular strength of the pharmacological activity of the drug, release rate and period of the drug and the like. For example, the polymer is used in an amount of 0.5 to 1,000 times the weight of the drug. Preferably, the polymer in an amount of about 1 to 100 times the weight of the drug is used.

The weight-average molecular weight of the polymer to be used may be selected from the range of about 3,000 to 30,000, preferably about 5,000 to 25,000 more preferably about 5,000 to 20,000.

The dispersity of the polymer to be used may be selected from the range of about 1.2 to 4.0, preferably about 1.5 to 3.5, more preferably about 1.5 to 2.5.

The weight-average molecular weight and dispersity in the present specification are determined by gel permeation chromatography (GPC).

Examples of the polymer in the present invention include biodegradable polymers such as poly fatty acid esters [e.g., homopolymers (e.g., polylactic acid, etc.) of fatty acids or copolymers (e.g., copolymer of lactic acid/glycolic acid, copolymer of 2-hydroxy burytic acid/glycolic acid, etc.) of two or more fatty acids, a mixture of the homopolymer and/or copolymer (e.g., a mixture of poly actic acid and copolymer of 2-hydroxybutyric acid/glycolic acid, etc.)]. Examples of the fatty acid include α-hydroxycarboxylic acid (e.g., glycolic acid, lactic acid, 2-hydroxy burytic acid, 2-hydroxyvaleric acid, 2-hydroxy-3-methyl burytic acid, 2-hydroxycaproic acid, 2-hydroxyisocaproic acid, 2-hydroxycaprylic acid, etc.), cyclic dimers of α-hydroxycarboxylic acids (e.g., glycolide, lactide, etc.), hydroxydicarboxylic acid (e.g., malic acid, etc.), hydroxytricarboxylic acid (e.g., citric acid, etc.), and so on. Further examples of the polymers include poly-α-cyanoacrylate, polyalkylene oxalates (e.g., polytrimethylene oxalate, polytetramethylene oxalate, etc.), poly ortho esters, poly ortho carbonates and other polycarbonates (e.g., polyethylene carbanate, polyethylenepropylene carbonate, etc.), polyamino acids (e.g., poly-γ-benzyl-L-glutamic acid, poly-L-alanine, poly-γ-methyl-L- glutamic acid, etc.) and the like. Further examples of the biocompatible polymers include polyacrylic acid, polymethacrylic acid, copolymer of acrylic acid and methacrylic acid, polyamino acids, silicone polymers, dextran stearate, ethylcellulose, acetylcellulose, maleic anhydride copolymers, ethylene-vinylacetate copolymer, polyvinyl acetate, polyvinyl alcohol, polyacrylamide and the like. These polymers may be used alone or in combination thereof. They may be used in the form of a copolymer or mere mixture of these two or more polymers. They may be in the form of salts thereof.

Among these polymers, in particular, poly fatty acid esters and poly-α-cyanoacrylate are preferred. Most preferred examples include poly fatty acid esters.

Among these poly fatty acid esters, in particular, homopolymers of α-hydroxycarboxylic acids, cyclic dimers of α-hydroxycarboxylic acid, copolymers of two or more α-hydroxycarboxylic acids, cyclic dimers of α-hydroxycarboxylic acid and a mixture of the homopolymers and/or the copolymers are preferred. More preferred examples include homopolymers of α-hydroxycarboxylic acids, copolymers of two or more α-hydroxycarboxylic acids, and a mixture of the homopolymers and/or the copolymers. Most preferred examples include polylactic acid, copolymer of lactic acid and glycolic acid, copolymer of 2-hydroxybutyric acid and glycolic acid and mixtures thereof.

When these α-hydroxycarboxylic acids, cyclic dimers of α-hydroxycarboxylic acids, hydroxydicarboxylic acid, hydroxytricarboxylic acids may be D-, L- or D,L-configured, the D-, L- and D,L-compounds can be used equally.

When a copolymer of lactic acid/glycolic acid is used as the above polymer, its composition (monomer) ratio is preferably about 100/0 to 50/50 (w/w). When a copolymer of 2-hydroxybutyric acid/glycolic acid is used as the above polymer, its composition (monomer) ratio is preferable about 100/0 to 25/75 (w/w).

The weight-average molecular weight of the copolymers of lactic acid/glycolic acid and the copolymer of 2-hydroxybutyric acid/glycolic acid is preferably about 3,000 to 30,000, more preferably about 5,000 to 20,000.

When a mixture of a polylactic acid (A) and a copolymer of 2-hydroxybutyric acid/glycolic acid (B) is used as one example of the above polymers, the mixture can be used in a blend ratio of about 10/90 to 90/10 (by weight), preferably about 25/75 to 75/25 (by weight).

The weight-average molecular weight of the polyactic acid (A) is preferably about 3,000 to 30,000, more preferably about 5,000 to 20,000.

The preferred proportion of glycolic acid in the copolymer (B) is in the range of about 40 to 70 mole %.

The weight-average molecular weight of the copolymer (B) is preferably about 5,000 to 25,000, more preferably about 5,000 to 20,000.

The microparticle preparation of the present invention can be prepared, for example, by the process which comprises spraying a solution of a polymer containing a drug and an aqueous solution of an agent for preventing aggregation of the microparticles separately from different nozzles and contacting them with each other in a spray dryer.

In the production of the microparticle preparation of the present invention, when a drug is water-soluble, the drug is dissolved in water by adding it to water to prepare an aqueous solution for an internal aqueous phase. As a pH adjustor to maintain the stability or solubility of the water-soluble drug, for example, carbonic acid, acetic acid, oxalic acid, citric acid, tartaric acid, succinic acid, phosphoric acid, sodium salt or potassium salt thereof, hydrochloric acid, sodium hydroxide or the like can be added to the aqueous solution. Further, as a stabilizer of the water-soluble drug, there can be added, for example, albumin, gelatin, citric acid, sodium ethylenediamine tetraacetate, dextrin, sodium hydrogensulfite or the like. Furthermore, as a preservative, there can be added, for example, paraoxybenzoic acid esters (e.g., methylparaben, propylparaben, etc.), benzyl alcohol, chlorobutanol, thimerosal or the like.

The solution for the internal aqueous phase thus obtained is added to a solution (oil phase) containing the polymer, followed by emulsification to prepare a W/O type emulsion.

As the solution containing the above polymer, a solution of the polymer dissolved in an organic solvent is used.

As the organic solvent, there can be used any solvent whose boiling point is nos more than about 120° C. and which is slightly miscible with water and can dissolve the polymer. Examples thereof include halogenated alkanes (e.g., dichloromethane, chloroform, chloroethane, trichloroethane, carbon tetrachloride, etc.), fatty acid esters (e.g., ethyl acetate, butyl acetate, etc.), ethers (e.g., ethyl ether, isopropyl ether, etc.), hydrocarbons (e.g., cyclohexane, n-hexane, etc.), aromatic hydrocarbons (e.g., benzene, toluene, etc.) and the like. These solvents can be used alone or in combination thereof.

The emulsification can be carried out by conventional dispersion techniques. For example, intermittent shaking, mixing by means of a mixer such as a propeller agitator, turbine agitator or the like, colloid mill operation, mechanical homogenization, ultrasonication and the like.

Alternatively, the drug (which may be water-soluble or fat-soluble) and polymer are dissolved in an organic solvent or a mixture of a solvent miscible with water and water. When the drug is insoluble, The mixture is subjected to a suspending operation to prepare a S/O type suspension containing finely divided drug particles. As the organic solvent in this case, in addition to the aforementioned organic solvents, there can be used solvents readily miscible with water such as acetone, acetonitrile, tetrahydrofuran, dioxane, pyridine, alcohols (e.g., methanol, ethanol, etc.) or the like. These solvents can be used alone or in combination thereof. Further, there can be used a mixture having a suitable mixing ratio of water and the above organic solvent which can dissolve the drug and polymer homogeneously.

Then, the W/O type emulsion, S/O type suspension or solution thus obtained, is sprayed into a drying chamber of a spray dryer through a nozzle, and the organic solvent and water in the atomized droplets are volatilized in an extremely short period of time to prepare powdered microparticle preparation. As the nozzle, a two-liquid type nozzle, pressure type nozzle, rotary disc type nozzle or the like can be used. At the same time, in order to prevent aggregation of the microparticles, an aqueous solution of an aggregation-preventing agent is sprayed from another nozzle. Namely, two nozzles are provided, and the W/O type emulsion, S/O type suspension or drug polymer solution is sprayed from one nozzle, while a suitable amount of an aqueous solution of an aggregation-preventing agent is sprayed from the other nozzle to form a coating on the surface of the microparticles. When a two-liquid nozzle or pressure nozzle is used as the nozzle, the two nozzles may be provided in the center of a spray dryer. Preferably, a nozzle having structure for two-liquid spraying is used so that the drug-polymer solution and aqueous solution of the aggregation-preventing agent can be sprayed separately without mixing them in the nozzle.

The microparticle preparation thus obtained is subjected to removal of the water and the solvent in the microparticle preparation. If necessary, with warming. The particle size of the microparticle preparation depends upon the desired degree of prolonged release. When the particles is used as a suspension, the particle size can be in the range which satisfies their dispersibility and needle pass requirements. For example, the average diameter is preferably in the range of about 0.5 to 400 μm, more preferably about 2 to 200 μm.

Thus, according to the process of the present invention, the takeup ratio of the drug into the microparticle preparation can be increased up to about 100% without any loss of the active component which is apt to provide in the in-water drying process. Further, the amount of the organic solvent to be used is smaller than that of the in oil drying process. Furthermore, although it takes an extremely long period of time to remove the solvent in the in-water drying process, this time can be drastically reduced. Thus, the process of the present invention is extremely useful in the industrial production.

Further, the microparticle preparation of the present invention has many advantages. For example, because the surface of the microparticles is coated with the aggregation-preventing agent in the form of a film, aggregation of the microparticle preparation is minimized in the course of production, and even globular microparticle preparation can be obtained. Further, it is easy to control the solvent removal step, and thereby the surface structure of the microparticle preparation which affects the drug release rate (e.g., the number and size of pores which are main release path of the drug, etc.) can be controlled.

The microparticle preparation of the present invention can be administered as it is into the living bodies as implants, or by molding them in the form of various preparations. Further, the microparticle preparation can be used as raw materials in the production or various preparations.

As the above preparation, for example, injectable preparations, oral preparations (e.g., powders, granules, capsules, tablets, etc.), nasal preparations, suppositories (e.g, rectal, vaginal), and so on are also possible.

The amount of drug to be included in the preparation depends on the kind of the drug, dosage form, object of treatment, and so on. However, the amount of drug per dosage from may ususally be selected from the range of about 0.001 mg to about 5 g, preferably about 0.01 mg to about 2 g.

These preparations can be manufactured by using per se known methods in the field of pharmaceutics.

When the microparticle preparation according to this invention are to be processed into an injectable preparation, they are dispersed in an aqueous vehicle together with a dispersing agent (e.g., Tween 80, HCO-60 (Nikko Chemicals), carboxymethylkcellulose, sodium alginate, etc.), preservative (e.g, methyl-paraben, propyl-paraben, benzyl alcohol, chlorobutanol, etc.), isotonizing agent (e.g., sodium chloride, glycerin, sorbitol, glucose, etc.), etc. The vehicle may also be a vegetable oil (e.g., olive oil, sesame oil, peanut oil, cottonseed oil, corn oil, etc.), propylene glycol or the like. In this manner, a prolonged release injection can be produced.

When the microparticle preparation according to this invention are to be processed into an oral preparation, by per se known methods, they are mixed with an excipient (e.g., lactose, sucrose, starch, etc.), disintegrating agent (e.g., starch, calcium carbonate, etc.), binder (e.g., search, gum arabic, carboxymethylkcellulose, polyvinylpyrrolidone, hydroxypropylcellulose, etc.) or/and lubricant (e.g., talc, magnesium stearate, polyethyleneglycol 6000, etc.), and the mixtures are compressed in molds. If necessary, the preparations may be coated by per se known methods for the purpose of masking of the taste or providing them with enteric or sustained release property. Usable coating agents are, for example, hydroxypropylmethylcellulose, ethylcellulose, hydroxymethylcellulose, hydroxypropylcellulose, polyoxyethylene glycol, tween 80, Pluornic F68, celluloe acetate phthalate, hydroxypropylmethylcellulose phthalate, hydroxymethylcellulose acetate succinate, Eudragit (Roehm, West Germany; methacrylic acid-acrylic acid copolymer) and pigments such as titanium oxide and ferric oxide.

To manufacture a nasal preparation from the microparticle preparation according to the present invention, they are provided in a solid, semi-solid or liquid state in the conventional manner. To manufacture the solid nasal preparation for instance, the microcapsules either as they are or together with an excipient (e.g., glucose, mannitol, starch, microcrystalline cellulose, etc.) and/or thickener (e.g., natural mucilages, cellulose derivatives, polyacrylates, etc.) are processed into a powdery composition. To make a liquid composition, the microcapsules are processed into an oily or aqueous suspension in substantially the same manner as in the case of injections. The semi-solid preparation may be an aqueous or oily gel or ointment. In any case, there may be added a pH adjusting agent (e.g., carbonic acid, phosphoric acid, citric acid, hydrochloric acid, sodium hydroxide, etc.), a preservative (e.g., p-hydroxybenzoic acid esters, chlorobutanol, benzalkonium chloride, etc.), etc.

A suppository of the microparticle preparation according to the present invention, whether in an oily or aqueous solid or semi-solid state or a liquid state, can be produced in the per se conventional manner. The kind of oleagenous base for such composition is optional only if it will not dissolve the microcapsules. Thus, for example, higher fatty acid glycerides [e.g., cacao butter, Witepsol (Dynamit-Novel, Germany), etc.], intermediate fatty acids [e.g., Miglyol (Dynamit-Novel), etc.] and vegetable oils (e.g., sesame oil, soybean oil, cottonseed oil, etc.) may be mentioned. The aqueous base is exemplified by polyethylene glycol and propylene glycol, while the aqueous gel base may be selected from among natural mucilages, cellulose derivatives, vinyl polymers, polyacrylates, etc.

The dosage of the preparation according to the present invention depends on the kind and amount of the active ingredient, dosage form, druation of drug release, recipient animal (e.g., warm-blooded animals such as mouse, ran, horse, cattle or man), and object of treatment. It is, however, sufficient to ensure that the effective dose of the active ingredient will be administered. For example, the amount per dose to humans may be selected from the range of about 1 mg to 10 g, preferably about 10 mg to 2 g, in terms of the weight of microcapsules.

When an injectable dosage form is employed, the volume of the suspension may be selected from the range of about 0.1 to 5 ml, preferably about 0.5 to 3 ml.

The polymer as a base for the microparticle preparation in the present invention can be produced by per se known methods such as the methods described in U.S. Pat. Nos. 3,773,919, 4,273,920, 4,675,189, 4,767,628, 4,677,191, 4,849,228 or EP-A-481732.

The microparticle preparation of the present invention has, for example, the following characteristics.

(1) The prolonged release of drugs in various dosage forms can be ensured. In particular, when a long-term treatment with injections is required for the desired effect, the preparation helps achieve the desired pharmacological activities stably with an administration schedule of once a week or a month or even once a year, instead of giving injections every day. Thus, compared with the conventional sustained release drugs, the prolonged release preparation of the present invention ensure longer sustained effects.

(2) When the injectable preparations are prepared by using the microparticle preparation of the present invention, any surgical operation such as implantation is not required. The preparations can be administered subcutaneously or intramuscularly in quite the same manner as in the conventional injectable suspensions, and it is not required to remove them from the body.

Further, the injectable preparations can be administered directly to the tumor itself, the site of inflammation or the receptor region, so that systemic side effects can be controlled and the drug can be allowed to efficiently act on the target organ over a longer period of time, thus making for increased drug efficacy. Furthermore, the injectable preparations can be used in intra-arterial administration in the vascular embolic therapy proposed by Kato et al., of cancer of the kidney and of the lung [Lancet II, pp. 479–480 (1979)].

(3) The release of the active component is continuous and, in the case of hormone antagonists, receptor antagonists or the like, stronger pharmacological activities are obtained than possible by daily administration.

(4) A drug can be entrapped into the microparticle preparation more efficiently than those obtained by the conventional in water drying of the W/O/W type three-phase emulsion. Further, finely divided or even globular microparticle preparation can be obtained.

(5) The microparticle preparation having a drug content of 10 to 50% which are hardly obtainable by the conventional in-water drying process can be obtained.

(6) Since, compared with the conventional in-water drying process, a solvent removal rate is higher, the hardening rate of the microparticle preparation is higher and the microparticle preparation having a stronger structure can be obtained. Therefore, the initial drug release rate after administration can be reduced.

(7) Aggregation and adhesion of the microparticle preparation is remarkably diminished compared with spraying a solution containing only the drug and the polymer.

The following experiments and examples further illustrate the present invention in detail, bus are not to be construed to limit the scope thereof. All the percents representing the concentration are weight/volume percents (w/v %) unless otherwise stated.

Experiment 1

Leuprorelin acetate (1 g) was dissolved in water (10 ml) at 60° C. To this solution was added a solution of lactic acid-glycolic acid copolymer (lactic acid/glycolic acid=75/25, average molecular weight calculated in terms of polystyrene: 1,200) (9 g) dissolved in methylene chloride (125 ml). The mixture was emulsified with a small-sized homogenizer (Polytron, manufactured by Kinematica, Switzerland) to obtain a W/O type emulsion.

(1) In-water drying process (the conventional method, hereinafter referred to as A process)

The above W/O type emulsion was converted into a (W/O)/W type emulsion in 0.5% PVA aqueous solution (500 ml) by using a homogenizer. Then, the emulsion was stirred slowly for 3 hours with a conventional propeller agitator. As methylene chloride was volatilized, (W/O) type microcapsules were hardened and, then, the resulting microcapsules were collected by centrifugation. At the same time, the microcapsules were washed with purified water. The collected microcapsules were subjected to freeze drying a whole day and night to obtain powder.

(2) Spray drying process (the present invention, hereinafter referred to as B process)

The above W/O type emulsion was sprayed from one nozzle of a two fluid nozzle at a flow rate of 10 ml/min and, at the same time, 2% aqueous mannitol solution was sprayed from the other nozzle at a flow rate of 10 ml/min into a drying chamber of a spray dryer to obtain microcapsules as powder. The temperature at the entrance of the drying chamber was 100° C., the temperature at the outlet was 50° C. and the air flow was 80 kg/hr.

Various properties of the microcapsules produced by A and B processes were compared. The results are shown in Table 1.

TABLE 1

Comparison of Properties of Microcapsules

| Process | Surface state | Drug takeup [1] (%) | Release rate for 1 day [2] (%) | Distribution of particle size [3] (μm) |
|---|---|---|---|---|
| A | many pores | 5.3 | 78 | 5-200 |
| B | few pores | 99 | 24 | 5-40 |

[1] Drug take up was determined as follows.

1) Drug take up was determined as follows.

The leuprolide acetate in the microcapsules was determined by a high performance liquid chromatography (HPLC) procedure using Hitachi L-6300 equipment (Hitachi, Japan), microcapsules (50 mg) were dissolved in a mixture of ml of dichloromethane and 20 ml of 1/30M phosphate buffer, pH 6.0, and leuprolide acetate extracted into the buffer was assayed by an HPLC procedure with an ultra violet (UV) detector under the following conditions; column, Lichrosorb RP.18 250 mm in length with 4 mm i.d.; column temperature, 30° C.; mobile phase, a mixture of 100 ml of 0.25M acetonitrile and 150 ml of methyl alcohol; flow rate, 0.7 ml/min; wavelength, 280 nM.

Drug take up (%) was calculated from the following formula;

$$\text{Drug take up (\%)} = \frac{\text{The leuprolide acetate in the microcapsole}}{\text{Initial amount of Leuprolide acetate added}} \times 100$$

2) Release rate for 1 day (%) was determined as follows.

The microcapsules (50 mg) were suspended in 10 ml of the release medium consisting of 1/30M phosphate buffer, pH 7.0, containing 0.05% Tween-80 (Kao-Atlas, Tokyo) in a shaking bottle. This was shaken at 37° C. for 1 day by using a shaker (Taiyo Scientific Industrial Co., Tokyo).

The residual leuprolide acetate in the microcapsules was determined after filtering the microcapsules through a 0.8 μm Millipore filter by the analytical method mentioned 1).

Release rate for 1 day (%) was calculated from the following formula.

Release rate for 1 day (%) =

$$1 - \left( \frac{\text{The residual leuprolide acetate in the microcapsules}}{\text{The initial amount of leuprolide acetate in the microcapsules}} \right) \times 100$$

3) The distribution of particle size (μm) was determined as follows.

Microcapsules (10 mg) were suspended in Isoton II solution (Nikkaki Ltd., Japan). This suspension was subjected to a Multilizer (Coulter Inc. Co., U.S.A.) which was equipped with aperture tube of 100 μm or 280 μm to determine the distribution of particle size of the microcapsules.

As shown in Table 1, when the surface of the microcapsules was observed with a scanning electron microscope, many pores were observed on the surface of the microcapseles produced by the A process, whereas pores were hardly observed on the surface of the microcapsules produced by the B process and the surface was coated with mannitol homogeneously in the form of a film. The takeup of the drug, i.e., leuprorelin acetate was larger in the B process than in the A process. The amount of released drug for 1 day (initial release rate) in a release test of the microcapsules obtained by the B process was larger than that obtained by the A process.

The particle size distribution of the microcapsules obtained by the B process was sharper than that obtained by the A process. The time required for the production was about 24 hours in the A process, while it was extremely short and about 10 minutes in the B process. Thus, in view of the overall comparison, the B process is an extremely more useful production process of microcapsules than the A process.

Experiment 2

Thyrotropin-releasing hormone (TRH) (1.0 g) and lactic acid-glycolic acid copolymer (lactic acid/glycollic acid=75/25, average molecular weight: 16,000) (9.0 g) were dissolved homogeneously in a mixed solvent of acetone (30 ml) and water (3 ml). The solution was sprayed from one nozzle of 2 two-fluid nozzles set in the center of the spray dryer at a flow rate of 10 ml/min and, at the same time, 5% aqueous mannitol solution was sprayed from the other nozzle for the prevention of aggregation of the microcapsules to obtain microcapsules as powder. The TRH content in the microcapsules was 9.8% (takeup: 98%), and the initial release rate in M/30 phosphate buffer (pH 7.0, 37° C.) was 5%. The particle size distribution was 5 to 50 μm (average: 20 μm). The microcapsules were globular and had few pores on the surface.

EXAMPLE 1

α-interferon (500 mg) and gelatin (50 mg) were dissolved in water (300 mg) at 50° C. The solution was added to a solution of polylactic acid (molecular weight: 21,000) (3,500 mg) dissolved in methylene chloride (4 ml). The resulting mixture was homogenized with Plytron for 20 seconds to obtain a W/O type emulsion. The W/O type emulsion was injected into and sprayed from one (internal) of the rotary disc type nozzles having a dual structure and, at the same time, 2% aqueous mannitol solution containing 0.5% polyvinyl alcohol (PVA) was injected into and sprayed from the other (external) nozzle. After spray drying, the desired microcapsules were obtained as powder.

EXAMPLE 2

Methotrexate (1 g) and 2-hydroxybutyric acid-glycolic acid copolymer (2-hydroxybutyric acid/glycolic acid=50/50, average molecular weight: 10,000) (9 g) were dissolved in a mixed solution of water (5 ml) and acetonitrile (30 ml). The solution was sprayed from the most inner duct of the two fluid nozzle (three fluid nozzle) having a structure for two-liquid spraying. An aqueous solution of gelatin (1%) was passed through the middle duct and compressed air was passed through the most outer duct to atomize and spray the solution. Thus, the desired microcapsules were obtained.

EXAMPLE 3

Cefotiam dihydrochloride (4 g) and sodium carboxymethyl cellulose (Na-CMC) (600 mg) were dissolved in water (2 ml) at 60° C. The solution was mixed with a solution of polylactic acid (molecular weight: 30,000) (10 g) dissolved in chloroform (40 ml). The mixture was stirred to obtain a W/O type emulsion. The W/O type emulsion was sprayed from one of the two-fluid nozzles and, at the same time, 5% aqueous lactose solution was sprayed from the other nozzle to obtain the desired microcapsules.

EXAMPLE 4

A fat-soluble drug, DN-2327 (0.5 g) and lactic acid-glycolic acid copolymer (lactic acid/glycolic acid=75/25, average molecular weight: 10,000) (4.5 g) were dissolved in acetonitrile (15 ml). The solution was sprayed from one of the two-fluid nozzles and, at the same time, 5% aqueous mannitol solution was sprayed from the other nozzle to obtain the desired microcapsules.

As described hereinabove, the microparticle preparation of the present invention is a superior preparation having a high drug content, a reduced initial release rate of a drug and a sharp particle size distribution.

What is claimed is:

1. A process for the production of a microparticle preparation comprising spraying a solution of a polymer containing a drug and an aqueous solution of an agent for preventing aggregation of the microparticles separately from different nozzles and contacting them with each other in a spray dryer to produce microparticles of the polymer which contain the drug and are coated with a film of the agent for preventing aggregation of the microparticles.

2. A process according to claim 1, wherein the polymer solution containing the drug is a homogeneous solution.

3. A process according to claim 1, wherein the the polymer solution containing the drug is a W/O type emulsion whose internal phase is an aqueous solution containing the drug and whose external phase is a solution containing the polymer.

4. A process according to claim 1, wherein the polymer solution containing the drug is an S/O type suspension containing drug particles.

5. A process according to claim 1, wherein the polymer is a slightly water-soluble or water-insoluble biocompatible polymer having a weight-average molecular weight of about 1,000 to 800,000.

6. A process according to claim 5, wherein the polymer is biodegradable.

7. A process according to claim 6, wherein the polymer is a poly fatty acid ester.

8. A process according to claim 7, wherein the polymer is selected from the group consisting of polylactic acid, copolymer of lactic acid and glycolic acid, copolymer of 2-hydroxybutyric acid and glycolic acid and a mixture thereof.

9. A process according to claim 3, wherein the internal aqueous phase contains about 0.001% to about 70% (w/w) of the drug.

10. A process according to claim 1, wherein the drug is a member selected from the group consisting of biologically active peptides, antibiotics, antitumor agents, antipyretics, analgesics, antiinflamatory agents, antitissive expectorants, sedatives, muscle relaxants, antipiliptic agents, antiulcer agents, antidepressants, antiallergic agents, cardiotonics, antiarrhythmic agents, vasodilators, hypotensive diuretics, antidiabetic agents, anticoagulatns, hemostatics, antituberculous agents, hormone preparations and narcotic antagonists.

11. A process according to claim 1, wherein the agent for preventing aggregation is a water-soluble material which is applicable to human and is solid at room temperature and non-adhesive its dried state.

12. A process according to claim 11, wherein the agent is a member selected from the group consisting of water-soluble saccharides, amine acids, proteins and water-soluble cellulose.

13. A process according to claim 1, wherein the amount of the agent for preventing aggregation is about 0.1 to about 100 times the weight of the polymer.

14. A process according to claim 1, wherein the particle size is about 0.5 to 400 μm.

15. A process according to claim 1, wherein the microparticle preparation is a prolonged release microparticle preparation.

* * * * *